United States Patent [19]
Hope et al.

[11] Patent Number: 5,550,307
[45] Date of Patent: *Aug. 27, 1996

[54] INCREASED DIMER YIELD OF OLEFIN OLIGOMERS THROUGH CATALYST MODIFICATIONS

[75] Inventors: Kenneth D. Hope; Ting C. Ho; Barrett L. Cupples, all of Kingwood, Tex.

[73] Assignee: Chevron Chemical Company, San Ramon, Calif.

[*] Notice: The term of this patent shall not extend beyond the expiration date of Pat. No. 5,420,373.

[21] Appl. No.: 298,635

[22] Filed: Aug. 31, 1994

Related U.S. Application Data

[63] Continuation-in-part of Ser. No. 217,265, Mar. 24, 1994, Pat. No. 5,420,373.

[51] Int. Cl.$^6$ .................................................. C07C 2/14
[52] U.S. Cl. ........................ 585/525; 585/502; 585/510; 585/521
[58] Field of Search .................... 585/502, 510, 585/521, 525

[56] References Cited

U.S. PATENT DOCUMENTS

| | | | |
|---|---|---|---|
| 4,436,947 | 3/1984 | Morganson et al. | 585/525 |
| 5,068,487 | 11/1991 | Theriot | 585/510 |
| 5,095,172 | 3/1992 | Lanier et al. | 585/851 |
| 5,420,373 | 5/1995 | Hope et al. | 585/525 |

*Primary Examiner*—Shrive Beck
*Assistant Examiner*—Timothy H. Meeks
*Attorney, Agent, or Firm*—E. A. Schaal

[57] ABSTRACT

An oligomer is made by contacting an olefinic monomer with a catalyst comprising boron trifluoride, an alcohol alkoxylate, and a ketone. In one embodiment, the olefinic monomer is a straight-chain, α-olefinic monomer containing from 8 to 12 carbon atoms, the alcohol alkoxylate is 2-ethoxyethanol, the ketone is methyl ethyl ketone, and the oligomer product has a kinematic viscosity at 100° C. of less than 1.7 cSt. Before removal of unreacted monomer, the oligomer product is at least 50 wt. % dimer, at least 80 wt. % dimer plus trimer, and less than 3.25 wt. % tetramer and greater.

9 Claims, 2 Drawing Sheets

Boron trifluoride and
2-ethoxyethanol Catalyst
Oligomer Yields

Boron trifluoride and
2-butoxyethanol Catalyst
Oligomer Yields

1

INCREASED DIMER YIELD OF OLEFIN OLIGOMERS THROUGH CATALYST MODIFICATIONS

This application is a continuation-in-part of application Ser. No. 08/217,265, filed Mar. 24, 1994, U.S. Pat. No. 5,420,373, issued May 30, 1995 entitled "Controlled Formation of Olefin Oligomers," which is hereby incorporated by reference for all purposes.

The present invention relates to a process of producing dimers and trimers of olefins in significantly high yields.

BACKGROUND OF THE INVENTION

It is well known to make polyalphaolefins by reacting 1-decene with boron trifluoride and butanol. The oligomer product is a mixture of dimer, trimer, and higher molecular weight materials.

The market for the trimer and higher molecular weight materials is well established, both in military applications and in automotive and industrial uses that require a 4 centistoke (cSt) or greater kinematic viscosity. The dimer, which has a viscosity of about 2 cSt, was usually recycled to the reaction. That resulted in better economics but a somewhat poorer product performance. Because of the market demand for the trimer and higher molecular weight materials and lack of market demand for dimer production, most of the work in this area has involved minimizing the amount of dimers made.

The dimer is useful in heat transfer fluids, dielectric fluids, and lubricating fluids. Recently, it also has been found to be useful in drilling fluids. This involves replacing petroleum fractions, chiefly diesel oil, in oil-based drilling fluids with environmentally compatible polyalphaolefins. Oil-based drilling fluids are undesirable in off-shore petroleum exploration because those fluids produce an unwanted sheen on the water and are harmful to certain marine life. This new market for dimers has changed the economics of the industry. Now, there is an economic motivation to increase dimer yield, rather than minimize it.

U.S. Pat. No. 5,068,487 by Theriot discloses a process for producing oligomerization of olefins with boron trifluoride and alcohol alkoxylates to produce predominately dimer and trimer. Unfortunately, this process can create a highly viscous emulsion layer in the reactant and aqueous wash streams. These emulsions can cause operating difficulties, such as inhomogeneity in the reactor, process line plugging, poor product recovery, and lengthy phase separation times.

Previously, we filed an application U.S. Ser. No. 08/217,265 to the use of boron trifluoride in conjunction with hydroxy carbonyls. In one embodiment of that invention, a ketone was used as a copromoter with the hydroxy carbonyl to improve dimer yield.

U.S. Pat. No. 4,436,947 by Morganson et al. discloses oligomerization of $C_6$–$C_{20}$ olefins, such as 1-decene, with boron trifluoride and a mixture of an aliphatic alcohol, an aliphatic ketone, and a polyol to increase the trimer to tetramer ratio. The dimer to trimer and higher oligomer ratio of the examples varies from 0.09:1 to 0.19:1.

U.S. Pat. Nos. 4,436,947 and 5,068,487 are hereby incorporated by reference for all purposes.

SUMMARY OF THE INVENTION

The present invention provides a process for improving dimer yield and for eliminating an emulsion problem associated with the prior art. That process involves the use of ketone with a boron trifluoride and alcohol alkoxylate co-catalyst to oligomerize an olefinic monomer.

We have found that ketone not only helps boost dimer yields of catalyst systems of boron trifluoride and hydroxy carbonyls, but also helps boost dimer yields of catalyst systems of boron trifluoride and alcohol alkoxylates.

Preferably, the alcohol alkoxylate is either 2-ethoxyethanol or 2-butoxyethanol. More preferably, the alcohol alkoxylate is 2-ethoxyethanol.

Preferably, the ketone is methyl ethyl ketone.

Preferably, the olefinic monomer is a straight-chain, $\alpha$-olefinic monomer containing from 6 to 20 carbon atoms. More preferably, it contains predominately 8 to 12 carbon atoms.

Preferably, the oligomer product has a kinematic viscosity at 100° C. of less than 2.0 cSt. More preferably, the kinematic viscosity at 100° C. is less than 1.7 cSt.

The oligomer product should be predominately dimer and trimer, and the dimer to trimer and higher oligomer ratio should be at least 1:1. Preferably, before removal of unreacted monomer, the oligomer product is at least 50 wt. % dimer, at least 80 wt. % dimer plus trimer, and less than 3.25 wt. % tetramer and greater.

BRIEF DESCRIPTION OF THE DRAWINGS

In order to assist the understanding of this invention, reference will now be made to the appended drawings. The drawings are exemplary only, and should not be construed as limiting the invention.

DETAILED DESCRIPTION OF THE INVENTION

Figure 1:
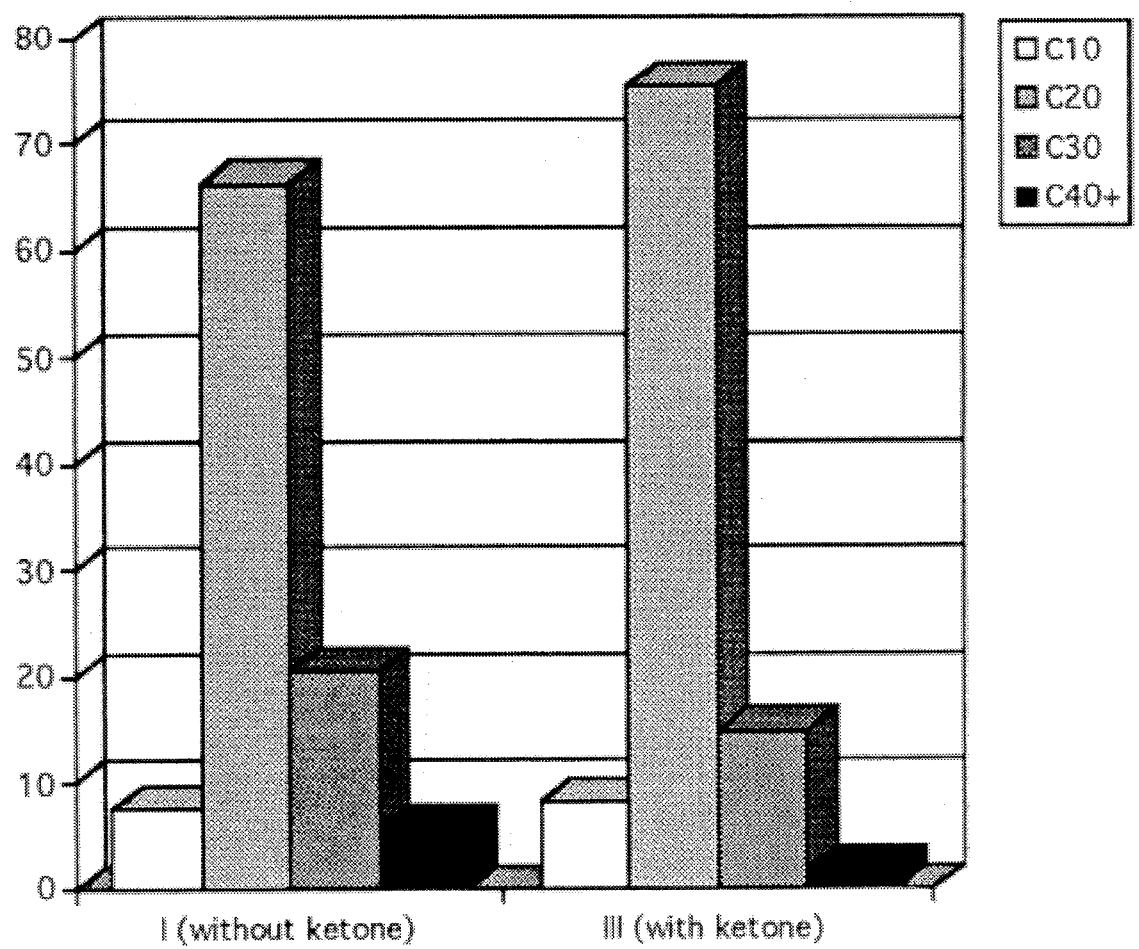
FIG. 1 shows oligomer yields for $BF_3$ and 2-ethoxyethanol catalyst systems (with and without the presence of methyl ethyl ketone).
Figure 2:
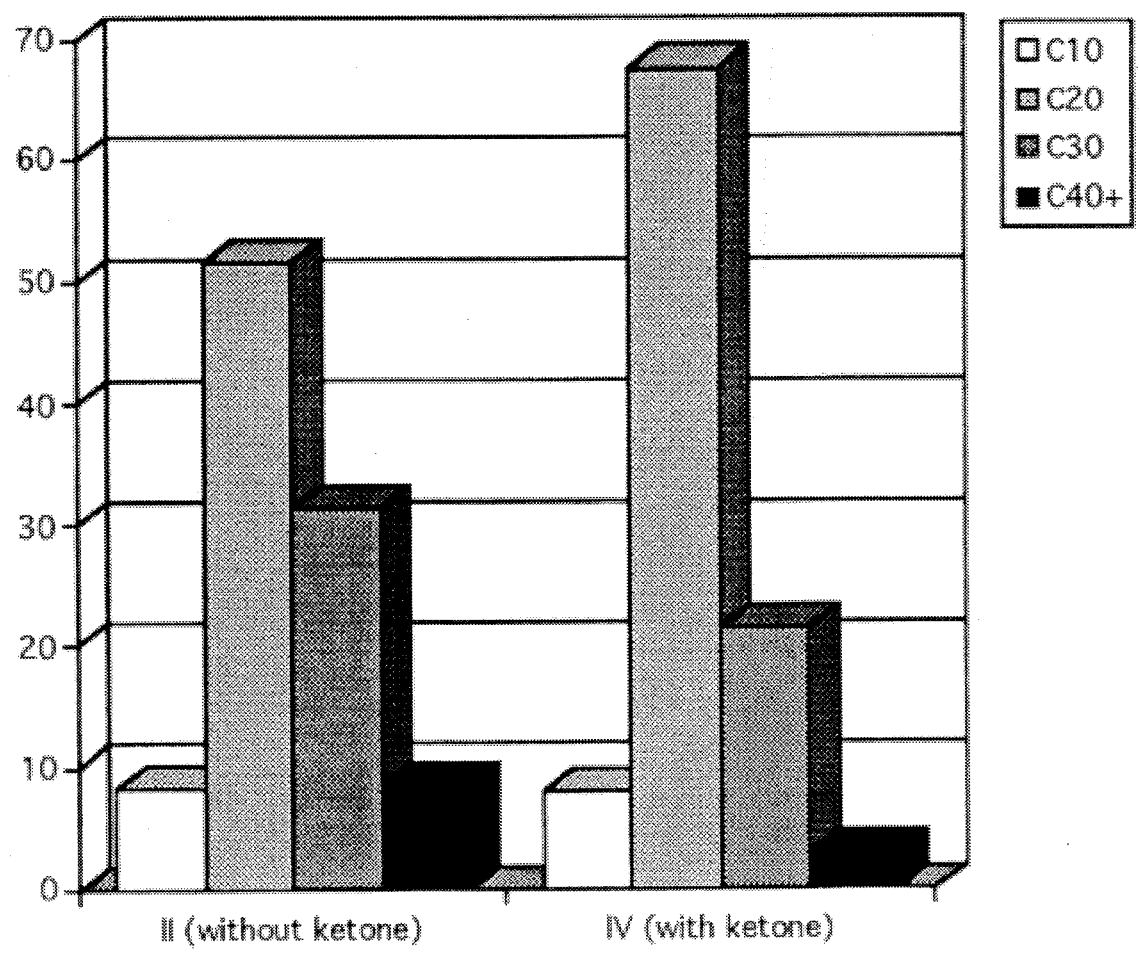
FIG. 2 shows oligomer yields for $BF_3$ and 2-butoxyethanol catalyst systems (with and without the presence of methyl ethyl ketone).

In its broadest aspect, the present invention involves the oligomerization of an olefinic monomer by contacting that monomer with boron trifluoride, an alcohol alkoxylate, and a ketone.

Preferably, the alcohol alkoxylate is either 2-ethoxyethanol or 2-butoxyethanol, more preferably 2-ethoxyethanol. Alcohol alkoxylates useful as promoters can be represented, for example, by the formula:

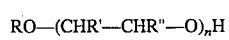

RO—(CHR'—CHR"—O)$_n$H where R is hydrocarbyl containing from 1 to 24 carbons, including mixtures thereof, R' and R" are independently hydrogen, methyl, or ethyl, and n averages 1 to 15. Such alcohol alkoxylates are disclosed in U.S. Pat. No. 5,068,487, entitled "Olefin Oligomerization With $BF_3$ Alcohol Alkoxylate Co-Catalysts," which has already been incorporated by reference.

OLEFINIC MONOMER

Preferably, olefins used in making the oligomer are predominately (at least 50 mole %) $C_6$–$C_{20}$ straight-chain, mono-olefinically unsaturated hydrocarbons in which the olefinic unsaturation occurs at the 1- or $\alpha$-position of the straight carbon chain. Straight-chain $\alpha$-olefins are preferred because they are more reactive and commercially available.

Such α-olefins can be made by the thermal cracking of paraffinic hydrocarbons or by the well known Ziegler ethylene chain growth and displacement on triethyl aluminum. Individual olefins may be used, as well as mixtures of such olefins. Examples of such olefins are 1-hexene, 1-heptene, 1-octene, 1-nonene, 1-decene, 1-dodecene, 1-hexadecene and 1-tetradecene. The more preferred normal-α-olefin monomers are those containing about 8 to 12 carbon atoms. The most preferred olefin monomers are 1-octene, 1-decene, and mixtures thereof. The olefin monomers can also contain minor amounts of up to about 50 mole %, and usually less than 25 mole %, of internal olefins and vinylidene olefins.

OLIGOMER PRODUCT

The oligomer product is that portion of the reaction product remaining after boron trifluoride, alcohol alkoxylate, ketone, and unreacted monomer are removed. When the olefinic monomer contains predominately 6 to 12 carbon atoms, the oligomer product preferably has a kinematic viscosity at 100° C. of less than 3.6 cSt. Preferably, the olefinic monomer contains predominately 8 to 10 carbon atoms, the oligomer product preferably has a kinematic viscosity at 100° C. of less than 2.0 cSt, more preferably less than 1.7 cSt.

Preferably, the oligomer product is predominately the dimer and trimer of the monomer. More preferably, at least 80 wt. % of the oligomer product is dimer and trimer before removal of unreacted monomer. Still more preferably, at least 90 wt. % of the oligomer product is dimer and trimer before removal of unreacted monomer. Preferably, the oligomer product is at least 50 wt. % dimer and less than 3.25 wt. % tetramer and greater before removal of unreacted monomer.

OLIGOMERIZATION REACTION

The alcohol alkoxylate and ketone are used in minor but effective amounts. For example, the total amount of alcohol alkoxylate and ketone used can be from about 0.001 to 0.04 moles per mole of monomer (0.1 to 4.0 mole percent). In general, the boron trifluoride is used in molar excess to the amount of promoter. This can be accomplished by using a closed reactor and maintaining a positive boron trifluoride pressure over the reaction mixture. The alcohol alkoxylate and ketone can be mixed with the olefin feed and the reaction can be carried out in a batch or continuous process at temperatures of about 0° to 200° C. and pressures ranging from atmospheric up to, for example, 1,000 psig. The reaction temperature will change the oligomer distribution, with increasing temperatures favoring the production of dimers. Preferred reaction temperatures and pressures are about 20° to 90° C. and 5 to 100 psig.

When a desired oligomer distribution is reached, the reaction is terminated by venting off excess boron trifluoride gas and purging with nitrogen gas to replace all boron trifluoride gaseous residue. The reaction product, unreacted monomer, and boron trifluoride-promoter complex residue are removed from the reactor for further processing. Some promoters can cause an undesirable emulsion layer formed between the reactor product and the boron trifluoride-promoter complex. Generally this emulsion has a higher viscosity than the reactor product and can form a coating on the walls of the reactor and transfer lines.

The reactor product is then washed with an aqueous caustic solution and followed by several water washes to ensure neutralization.

Prior art promoters, such as alcohol alkoxylates without ketones (U.S. Pat. No. 5,068,487), form emulsions in both the reactor and water wash. This can cause ineffective separation of the product from wash solutions and other operating difficulties such as equipment corrosion and plugging. Our catalyst system does not form any emulsions in either the reactor or the water wash.

The oligomer mixture from the reaction contains monomer, which can be removed by distillation. The monomer has been found to contain appreciable amounts of less reactive, isomerized material. However, this monomer can be recycled because it will react to form oligomers in the presence of fresh α-olefin monomer. For example, portions of up to about 25 wt. %, and preferably 5 to 15 wt. % recycled monomer, based on total monomer, can be mixed with fresh monomer. The product mixture can be further separated by distillation to provide one or more product fractions having the desired viscosities for use in various lubricant applications such as drilling, hydraulic or metal working fluids, gear oils and crankcase lubricants.

The oligomer product can be hydrogenated by conventional methods to increase the oxidation stability of the product. Supported nickel catalysts are useful. For example, nickel on a Kieselguhr support gives good results. Batch or continuous processes can be used. For example, the catalyst can be added to the liquid and stirred under hydrogen pressure or the liquid may be trickled through a fixed bed of the supported catalyst under hydrogen pressure. Hydrogen pressures of about 100 to 1,000 psig at temperatures of about 150° to 300° C. are especially useful.

EXAMPLES

The invention will be further illustrated by following examples, which set forth particularly advantageous method embodiments. While the Examples are provided to illustrate the present invention, they are not intended to limit it.

GAS CHROMATOGRAPHY METHOD

Hewlett-Packard Model 5710A gas chromatograph was used to analyze oligomer distribution of product samples in all the examples presented. The instrument had a ⅛×30-inch stainless steel packed column that contains Chromosorb PAW 80/100 mesh packing with 5% Dexsil 300 coating. The instrument was set up in the following oven temperature profile:

Initial temperature—150° C.

Ramp up rate—16° C. per minute

Final temperature—400° C.

Final time—16 minutes

Post temperature—100° C.

Post time—3 minutes

Comparative Example 1

BF$_3$ AND 2-ETHOXYETHANOL

The oligomerization reaction was carried out in an autoclave reactor. The reactor was equipped with a packless stirrer; and all wetted surfaces were made of 316 stainless steel. The reactor had an external electrical heater and an internal cooling coil for temperature control. The reactor was equipped with a dip tube, gas inlet and vent valves, and a pressure relief rupture disc. Prior to the monomer charge, the reactor was cleaned, purged with nitrogen and tested for leaks.

One thousand grams of 1-decene was charged into the reactor. The promoter, 2-ethoxyethanol, was added to a concentration of 0.25 wt. % based on feed. The entire reactor content was heated under nitrogen blanket to reach 75° C. When the reactor temperature reached equilibrium, the reactor was then evacuated to remove the nitrogen. Boron trifluoride gas was then sparged slowly with agitation in addition to cooling water circulating through the reactor cooling coil to avoid reactor temperature overrun. Additional boron trifluoride was added as necessary to maintain a reactor pressure of 20 psig. Small representative fluid samples were taken at 15, 30 and 60 minutes for gas chromatographic analysis. The reaction was terminated after two hours by venting off excess boron trifluoride gas and purging with nitrogen gas to replace all boron trifluoride gaseous residue. The reaction product and unreacted monomer were removed from the reactor. The reactor product was then washed with a 4 wt. % aqueous sodium hydroxide solution followed by several water washes to ensure neutralization. During the wash steps, an emulsion layer at the organic and aqueous interface was observed when using some of the promoters. The product analysis after one hour reaction time is given in Table 1.

Comparative Example 2

BF$_3$ AND 2-BUTOXYETHANOL

The process of Example 1 was repeated except that the promoter was 2-butoxyethanol. The product analysis after one hour reaction time is given in Table 1.

EXAMPLE 3

BF$_3$, 2-ETHOXYETHANOL, METHYL ETHYL KETONE

The process of Example 1 was repeated except that methyl ethyl ketone was used in addition to primary promoter. The amount of secondary promoter used was 0.5 wt. % based on feed. The product analysis after one hour reaction time is given in Table 1.

EXAMPLE 4

BF$_3$, 2-BUTOXYETHANOL, METHYL ETHYL KETONE

The process of Example 2 was repeated except that methyl ethyl ketone was used in addition to primary promoter. The amount of secondary promoter used was 0.5 wt. % based on feed. The product analysis after one hour reaction time is given in Table 1.

TABLE 1

Improvement in Dimer Yield Using the Promoters of the Present Invention

| Example | Dimer (wt. %) | Trimer (wt. %) | Tetramer + (wt. %) | Calc. Visc. @ 100° C. (cSt) |
|---|---|---|---|---|
| 1 | 66.2 | 20.5 | 5.7 | 2.21 |
| 2 | 51.6 | 31.5 | 8.6 | 2.51 |
| 3 | 75.4 | 14.8 | 1.6 | 2.00 |
| 4 | 67.6 | 21.5 | 2.9 | 2.14 |

EXAMPLE 5

EMULSION TEST

An additional benefit of the methyl ethyl ketone is its freedom from emulsions in both the reactor and the quench and wash stages. Generally, a promoter which is predisposed toward formation of emulsions will be troublesome in both of these process areas.

A simple laboratory test method was used to detect the presence of emulsions. The method combines, in a 125 ml separatory funnel, 15 ml of unquenched oligomer reactor product and 20 ml of 4 wt. % NaOH solution. The separatory funnel is shaken vigorously to mix the phases well and then they are allowed to separate by settling. The presence of an interfacial layer observable between the hydrocarbon and aqueous layers having a thickness greater than 2 mm and persisting longer than five minutes is evidence of a stable emulsion. Emulsions have been observed to also form with other bases including KOH and NH4OH and the laboratory test may also be varied to substitute these agents for NaOH.

This emulsion test was applied to various reactor products. An emulsion was observed for runs when 2-ethoxyethanol was used as the promoter. Emulsions were not observed for runs when methyl ethyl ketone was used as a secondary promoter.

While the present invention has been described with reference to specific embodiments, this application is intended to cover those various changes and substitutions that may be made by those skilled in the art without departing from the spirit and scope of the appended claims.

What is claimed is:

1. A process for making an oligomer comprising contacting an olefinic monomer with a catalyst comprising boron trifluoride, an alcohol alkoxylate, and a ketone.

2. A process according to claim 1 wherein the alcohol alkoxylate is selected from the group consisting of 2-ethoxyethanol and 2-butoxyethanol.

3. A process according to claim 2 wherein the alcohol alkoxylate is 2-ethoxyethanol.

4. A process according to claim 1 wherein the ketone is methyl ethyl ketone.

5. A process according to claim 1 wherein the olefinic monomer is a straight-chain, α-olefinic monomer containing from 6 to 20 carbon atoms.

6. A process according to claim 5 wherein the olefinic monomer contains 8 to 12 carbons atoms.

7. A process according to claim 6 wherein the oligomer product has a kinematic viscosity at 100° C. of less than 2.0 cSt.

8. A process according to claim 7 wherein the oligomer product has a kinematic viscosity at 100° C. of less than 1.7 cSt.

9. A process according to claim 1 wherein, before removal of unreacted monomer, the oligomer product is at least 50 wt. % dimer, at least 80 wt. % dimer plus trimer, and less than 3.25 wt. % tetramer and greater.

* * * * *